United States Patent [19]

Bolhofer et al.

[11] 4,420,615
[45] Dec. 13, 1983

[54] SUBSTITUTED PYRIDOPYRIMIDINES AS GASTRIC SECRETION INHIBITORS

[75] Inventors: William A. Bolhofer, Frederick; Edward J. Cragoe, Lansdale; Jacob M. Hoffman, Jr, North Wales, all of Pa.

[73] Assignee: Merck & Co., Inc., Rahway, N.J.

[21] Appl. No.: 295,930

[22] Filed: Aug. 24, 1981

[51] Int. Cl.³ ................. C07D 471/14; A61K 31/495
[52] U.S. Cl. ..................................... 544/279; 424/250; 424/251; 424/248.5; 424/248.4; 544/117; 544/61
[58] Field of Search ........................................ 544/279

[56] References Cited

U.S. PATENT DOCUMENTS

| | | | |
|---|---|---|---|
| 3,272,816 | 9/1966 | Papesch | 544/279 |
| 3,873,545 | 3/1975 | Osselaere et al. | 544/279 |
| 4,009,166 | 2/1977 | Noda et al. | 544/279 |
| 4,133,885 | 1/1979 | Bolhofer et al. | 544/126 |
| 4,215,216 | 7/1980 | Scotese et al. | 546/123 |
| 4,324,893 | 4/1982 | Scotese et al. | 544/279 |

Primary Examiner—Donald G. Daus
Assistant Examiner—S. A. Gibson
Attorney, Agent, or Firm—Gabriel Lopez; Salvatore C. Mitri; Hesna J. Pfeiffer

[57] ABSTRACT

There are disclosed novel substituted pyridopyrimidine compounds and processes for preparing such compounds. These compounds are useful as gastric secretion inhibitors in mammals.

8 Claims, No Drawings

SUBSTITUTED PYRIDOPYRIMIDINES AS GASTRIC SECRETION INHIBITORS

BACKGROUND OF THE INVENTION

Many heterocyclic compounds of widely diverse structure have been shown to be capable of inhibiting gastric acid secretion. In such compounds, antisecretory activity is dependent upon all the structural features of the molecule and their appropriate combination with the heterocyclic nucleus.

Of these compounds, those that appear to be most relevant to the present invention are represented by naphthyridinone compounds, disclosed in U.S. Pat. No. 4,133,885, and a pyrido-[2,3-d]pyrimidone carboxylic acid derivatives, disclosed in U.S. Pat. No. 4,215,216. However, these prior art compounds do not suggest the aminoalkyl pyridopyrimidine compounds of this invention.

The pyridopyrimidine compounds of this invention exhibit considerable activity for suppression of gastric acid secretion and are thus useful in peptic ulcer therapy and other hypersecretory conditions.

SUMMARY OF THE INVENTION

This invention is directed to substituted pyridopyrimidine compounds and to methods for preparing such compounds which compounds are useful for inhibiting gastric secretion in mammals.

DESCRIPTION OF THE INVENTION

The compounds of this invention are represented by the following structural formulae:

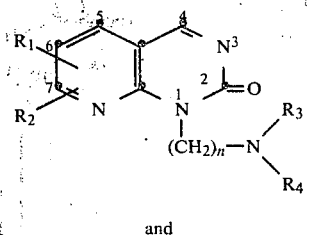
(I)

and

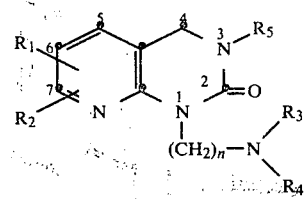
(II)

wherein, in each of Formulae I and II, $R_1$ and $R_2$ are independently hydrogen, haloalkyl loweralkyl, loweralkoxy;

$R_3$ and $R_4$ are independently hydrogen, loweralkyl, cycloloweralkyl, or $R_3$ and $R_4$ may be joined, together with the nitrogen to which they are attached, to form a 5- or 6-membered ring which can also include O, S, or N—$R_5$, is as defined below, to form a morpholine, thiomorpholine, or N-alkyl piperazine ring;

$R_5$ is hydrogen or loweralkyl;

n is 2-5; and, the physiologically acceptable salts thereof.

In the present invention, unless specified otherwise, the term "loweralkyl" includes alkyl groups containing 1-5 carbon atoms normal to branched. Examples of such alkyl groups include, but are not limited to, methyl, ethyl, propyl, iso-propyl, butyl, sec-butyl, pentyl, and the like.

The term "loweralkoxy" includes alkoxy containing 1-6 carbon atoms and the term "halo loweralkyl" represents such compounds as trifluoromethyl.

Preferred compounds of Formulae I and II are realized when $R_1$ is in the 5-position and $R_2$ is in the 7-position on the naphthyridine ring.

Further preferred compounds of Formulae I and II are those wherein n=2.

Most preferred compounds of Formulae I and II are those wherein $R_1$ and $R_2$ are methyl.

The compounds according to the invention readily form physiologically acceptable salts. Such salts include salts with inorganic acids such as hydrochlorides, hydrobromides, sulfates, nitrates and phosphates. Particularly useful salts of organic acids are formed with aliphatic mono- or dicarboxylic acids. Examples of such salts are acetates, maleates fumarates, tartrates, citrates, benzoates, succinates and isothionates. The compounds and their salts may also form hydrates and solvates.

The compounds represented by Formulae I and II have been found to have pharmacological activity in the animal body. For example, they have been found to inhibit secretion of gastric acid in the stomach of chronic fistula dogs at doses of from 1 to 20 mg per kilogram orally.

The pharmaceutical carrier employed may be for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like.

A wide variety of pharmaceutical forms can be employed. Thus, if a solid carrier is used, the preparation can be tableted, placed in a hard gelatin capsule in powder or pellet form, or in the form of a troche or lozenge. The amount of solid carrier will vary widely but preferably will be from about 15 mg to about 0.4 gm. If a liquid carrier is used, the preparation may be in the form of a syrup, emulsion, soft gelatin capsule, sterile injectable liquid such as an ampoule, or an aqueous or nonaqueous liquid suspension.

The pharmaceutical compositions are prepared by conventional techniques involving procedures such as mixing, granulating and compressing or dissolving the ingredients as appropriate to the desired preparation.

The active ingredient will be present in the composition in an amount effective to inhibit gastric acid secretory activity. The route of administration may be orally or parenterally.

Preferably, each daily dosage will contain the active ingredient in an amount of from about 500 mg to about 5000 mg, most preferably from about 1500 mg to about 3000 mg given in a single dose or multiple divided doses.

For therapeutic use, the pharmacologically active compounds of the present invention will normally be administered as a pharmaceutical composition comprising the compounds of this invention as the sole or an essential active ingredient in the basic form or in the form of an addition salt with a pharmaceutically acceptable acid and in association with a pharmaceutical carrier therefor. Such addition salts include those mentioned above.

The compounds of this invention can also be employed with other pharmacologically active compounds. Exemplary of such other pharmacological compounds are anticholinergic agents such as propantheline; Hl antihistamines such as mepyramine, pyribenzamine, chlorpheniramine, and the like; prostanoids such as prostaglandin El, prostaglandin A, and the like; histidine decarboxylase inhibitors such as α-fluoromethyl histidine, Brocresin (3-hydroxy-4-bromobenzyloxyamine), α-hydrazino histidine, and the like; antiulcer agents such as carbenoxolone, Vitamin U, and the like; antacids such as calcium carbonate preparations, aluminum hydroxide, and the like; nitrosation inhibitors such as Vitamine C; antigastrins such as somatostatin; as well as combinations and mixtures thereof.

Advantageously the composition will be made up in a dosage unit form appropriate to the desired mode of administration, for example as a tablet, capsule, or injectable solution.

The methods which can be employed to prepare the compounds of this invention are outlined in the following reaction schemes wherein $R_1$, $R_2$, $R_3$, $R_4$, $R_5$ and n are as defined above unless otherwise specified.

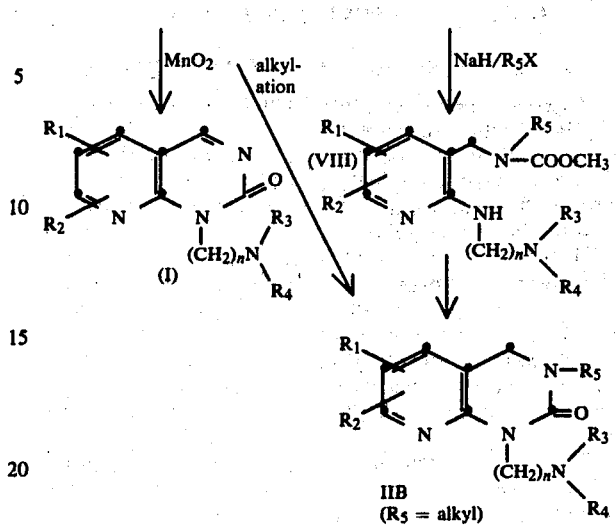

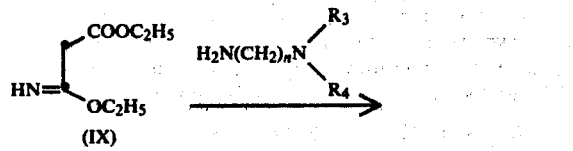

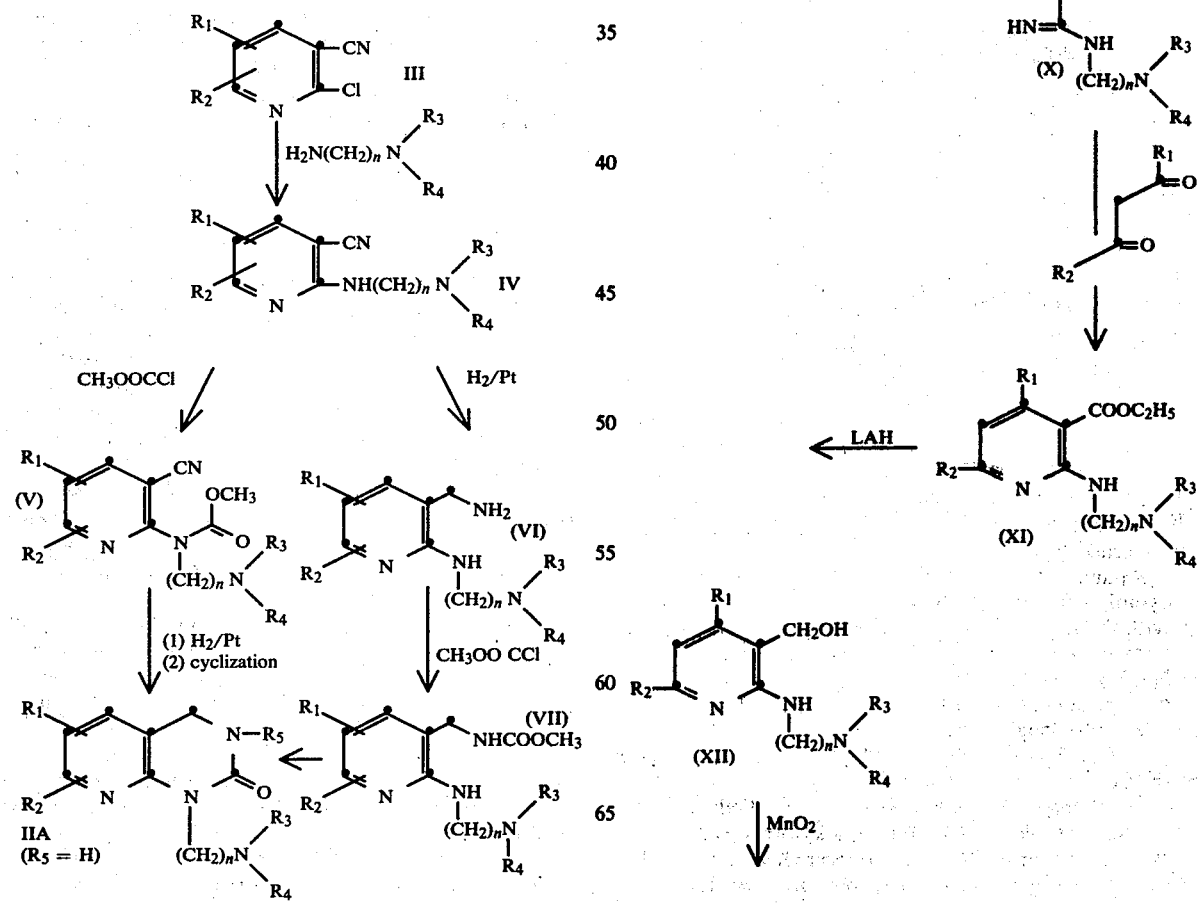

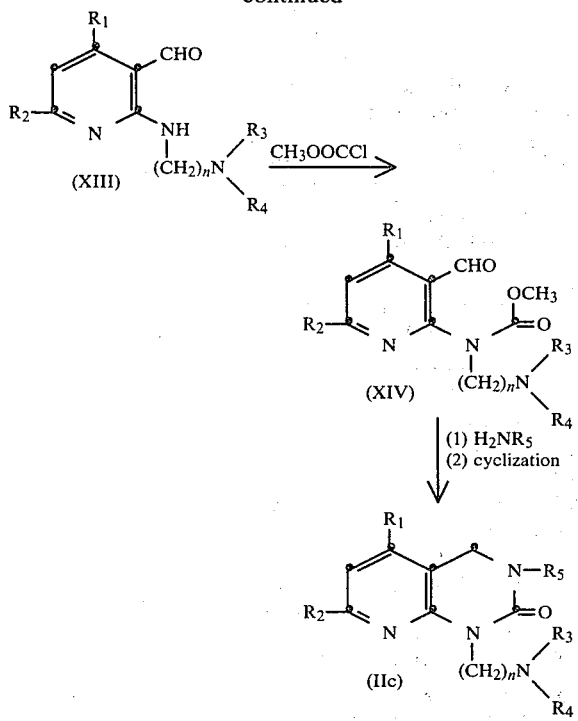

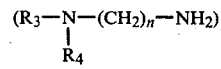

As shown in the foregoing Reaction Schemes, compounds I of the present invention can be made by oxidation (i.e. dehydrogenation) of IIA ($R_5$=H) using a selective oxidizing agent such as activated manganese dioxide in an aprotic solvent such as methylene chloride or benzene. Typically, the reaction mixture is heated at the boiling point of the solvent for 1-24 hours.

Compounds II of the present invention can be made by several methods: cyclization of the appropriately substituted pyridines VII or VIII, reductive cyclization of appropriate 3-cyano-pyridines V, or reductive amination-cyclization of appropriate pyridine carboxaldehydes XIV.

In the first instance, heating compound VII or VIII, ($R_5$=H, alkyl) at the boiling point of the selected solvent for 1-24 hours effects the cyclization to compound IIA and IIB, respectively. The preferred solvent is one which is weakly acid, such as, acetic acid.

Alternatively, a catalytic reduction of the cyano group of V to an aminomethyl with concomitant cyclization to compound IIA (R=H), can be carried out using, preferably, acetic acid as the solvent. This catalytic reduction-cyclization is carried out in a hydrogen atmosphere maintained at about 50 psi in the presence of a noble metal catalyst, preferably platinum, at room temperature for from 4-24 hours.

Compounds IIC ($R_5$=alkyl, $R_1$ is in position 5 and $R_2$ is in position 7) can be prepared by the reductive amination of an appropriate pyridine carboxaldehyde with an alkyl amine ($R_5NH_2$) under the typical reaction conditions described in the literature by Borch (J. Amer. Chem. Soc., 93, 2897-2904 (1971)). The alkylaminomethyl compound generated spontaneously cyclizes under the reaction conditions to give compound IIC (R=alkyl).

The intermediate cyanopyridine V can be made in two steps from substituted 2-chloro-3-cyano-pyridines (III). Reaction of III with an appropriate dialkylamino alkyl amine $$(R_3-\underset{\underset{R_4}{|}}{N}-(CH_2)_n-NH_2)$$

either in 100% excess amine or in the presence of an equivalent amount of tertiary amine such as triethylamine, is effected by heating at the boiling point of the lowest boiling amine component for 1-24 hours. The resultant aminopyridines (IV) are carboalkoxylated with a chloroformate ester such as methylchloroformate to give the cyanopyridines V. This reaction is carried out in an aprotic solvent, such as benzene, and the reaction mixture is refluxed for ½ to 3 hours. A tertiary amine, such as triethyl amine, can also be added to scavenge the hydrogen chloride generated. In this last reaction when $R_3$ and $R_4$ of compound IV are hindered alkyl groups, such as isopropyl, the reaction yield is very low and the following synthetic sequence is preferred.

Substituted pyridines of structure VII can be prepared from aminopyridines IV in two steps. The 3-cyano group of compound IV is catalytically reduced to give compound VI in a hydrogen atmosphere maintained at about 50 psi in the presence of a noble metal catalyst, such as platinum, and preferably in an acid medium, such as acetic acid. The reaction is generally carried out overnight, although shorter or longer times can be employed as necessary. The resultant 3-aminomethylpyridine VI is carboalkoxylated with methyl chloroformate in an aprotic solvent, such as benzene, in the presence of a tertiary amine, such as triethylamine, to scavenge the hydrogen chloride generated. The reaction is typically heated at reflux for 1-5 hours to give compound VII.

Pyridine carboxaldehydes (XIV) can be prepared by the carboalkoxylation of compounds XIII with methyl chloroformate under the reaction conditions described immediately above. The aldehyde XIII is obtained by the oxidation of alcohol XII with a selective oxidizing agent, such as activated manganese dioxide. The reaction is typically carried out at the boiling point of an aprotic solvent, such as methylene chloride or chloroform, for from 1-10 hours. The required alcohol XII is obtained by the standard lithium aluminum hydride (LAH) reduction procedure on ester XI in an ethereal solvent such as tetrahydrofuran.

A convenient preparation of esters XI involves a condensation between an appropriate 1,3-diketone, such as pentan-2,5-dione, and an aminoalkyl substituted amidinoacetate (X). The two component mixture is refluxed in an aprotic solvent such as benzene for from 10-24 hours.

The following examples are set forth to further illustrate the invention and describe preferred embodiments thereof, but are not to be construed as being limitative. Unless otherwise specified, all temperatures are in degrees Celsius.

EXAMPLE 1

1-(2-Diisopropylaminoethyl)-5,7-dimethyl-1,2,3,4-tetrahydropyrido[2,3-d]-pyrimidin-2-one

A.
N,N-Diisopropyl-N'-(3-cyano-4,6-dimethyl-2-pyridyl)-1,2-diaminoethane.

A mixture of N,N-diisopropyl-1,2-diaminoethane (10.8 g, 75 mmol) and 2-chloro-3-cyano-4,6-dimethylpyridine (12.5 gm, 75 mmol) in triethylamine (20 ml) is heated at 90° C. for 17 hours. The excess triethylamine is removed under vacuum and the residue is dissolved in chloroform, washed with water, dried over anhydrous sodium sulfate and evaporated to give essentially pure product (20.8 g) which is used in subsequent reactions. The title A product can be crystallized from methanol to give 13.6 g; m.p. 65°–68° C.

B.
N,N-Diisopropyl-N'-(3-aminomethyl-4,6-dimethyl-2-pyridyl)-1,2-diaminoethane A solution of N,N-diisopropyl-N'-(3-cyano-4,6-dimethyl-2-pyridyl-1,2-diaminoethane (15.1 g, 55 mmol) in glacial acetic acid (200 ml) containing platinum oxide catalyst (2.0 g) is hydrogenated in a Parr apparatus at room temperature over a 21 hour period. The catalyst is filtered and the solvent evaporated. This residue is dissolved in water, washed with chloroform, and then made basic with sodium carbonate and the product extracted into methylene chloride. This solution is dried and evaporated to give 10.1 g of oily title B product.

C. Methyl N-(2-diisopropylaminoethylamino-4,6-dimethyl-3-pyridylmethyl)carbamate To a solution of N,N-diisopropyl-N'-(3-aminomethyl-4,6-dimethyl-2-pyridyl)-1,2-diaminoethane (10.1 g, 36 mmol) in dry benzene (100 ml) is added methyl chloroformate (3.3 ml, 42 mmol) and then triethylamine (5.35 ml, 38 mmol). This mixture is gently refluxed for 1½ hours, cooled and the salts removed by filtration. The benzene solution is washed with water, dried and evaporated to give 11.3 g of code title C product.

D.
1-(2-Diisopropylaminoethyl)-5,7-dimethyl-1,2,3,4-tetrahydropyrido[2,3-d]-pyrimidin-2-one A solution of methyl N-(2-diisopropylaminoethylamino-4,6-dimethyl-3-pyridylmethyl)carbamate (12.0 g, 37 mmol) in glacial acetic acid (130 ml) is heated at reflux for 17 hours. The solvent is evaporated and the residue dissolved in water, washed with methylene chloride, and the aqueous solution made basic with sodium carbonate. The product is extracted into methylene chloride, dried and evaporated to give 8.9 g of crude product. Two recrystallizations from cyclohexane gives 3.5 g of crystalline title D product, m.p.: 135°–137° C.

EXAMPLE 2

1-(2-Diisopropylaminoethyl)-5,7-dimethyl-1,2-dihydropyrido[2,3-d]-pyrimidin-2-one A solution of 1-(2-diisopropylaminoethyl)-5,7-dimethyl-1,2,3,4-tetrahydropyrido[2,3-d]pyrimidin-2-one (3.5 g, 11.1 mmol) in methylene chloride (100 ml) containing activated manganese dioxide (9.0 g) is heated at reflux for 16 hours. The solution is filtered hot to remove the manganese dioxide and the manganese dioxide is extracted twice with hot chloroform. The organic extracts are combined, dried and evaporated to give 3.6 g of crude product which is crystallized from cyclohexane to give 2.0 g of pure title product; m.p.: 148°–150° C.

EXAMPLE 3

1-(2-Diisopropylaminoethyl)-3,5,7-trimethyl-1,2,3,4-tetrahydropyrido[2,3-d]pyrimidin-2-one

A. Methyl N-Methyl-N-(2-diisopropylaminoethylamino-4,6-dimethyl-3-pyridylmethyl)carbamate To a suspension of 50% sodium hydride in mineral oil (2.0 g, 42 mmol) in dry toluene (100 ml) under a nitrogen atmosphere is added a solution of methyl N-(2-diisopropylaminoethylamino-4,6-dimethyl-3-pyridylmethyl)carbamate (13.5 g, 40 mmol) in dry dimethyl sulfoxide (12 ml) and dry toluene (60 ml) in one portion. This mixture is stirred for one hour at room temperature and then methyliodide (2.52 ml, 40 mmol) is added dropwise. After stirring an additional three hours, acetic acid (6.0 ml) is added, followed by water. The aqueous layer is separated, washed with benzene and made basic with sodium carbonate. The product is extracted into methylene chloride, dried and evaporated to give 11.1 g of crude title A product.

B.
1-(2-Diisopropylaminoethyl)-3,5,7-trimethyl-1,2,3,4-tetrahydropyrido[2,3-d]pyrimidin-2-one A solution of methyl N-methyl-N-(2-diisopropylaminoethylamino-4,6-dimethyl-3-pyridylmethyl)carbamate (13.6 g, 38 mmol) in glacial acetic acid (100 ml) is heated at reflux for 20 hours. The solvent is evaporated and the residue dissolved in water, made basic with sodium carbonate and the crude product extracted into methylene chloride, dried and evaporated. This crude product (11.0 g) is chromatographed on silica gel using 10% methanol/chloroform as the eluent. The isolated title B product is crystallized twice from cyclohexane to give 3.0 g, m.p.: 97°–99° C.

EXAMPLE 4

1-(2-Dimethylaminoethyl)-5,7-dimethyl-1,2,3,4-tetrahydropyrido[2,3]pyrimidin-2-one

A.
N,N-Dimethyl-N'-(3-cyano-4,6-dimethyl-2-pyridyl)-1,2-diaminoethane

A mixture of 2-chloro-3-cyano-4,6-dimethylpyridine (10.0 g, 60 mmol) and N,N-dimethyl-1,2-diaminoethane (10.6 g, 120 mmol) is heated at 105° C. for 20 hours. Added benzene, evaporated to dryness, dissolved residue in water, made basic with sodium carbonate and extract product into methylene chloride, dried and evaporated to give 13.4 g of oily title A product.

B. Methyl N-(3-cyano-4,6-dimethyl-2-pyridyl)-N-(2-dimethylaminoethyl)carbamate To a solution of N,N-dimethyl-N'-(3-cyano-4,6-dimethyl-2-pyridyl)-1,2-diaminoethane (13.5 g, 62 mmol) in dry benzene (150 ml) is added methyl chloroformate (7.1 ml, 92 mmol) and then the resulting mixture is refluxed for 1½ hours. This mixture is evaporated to dryness and the residue dissolved in water, washed with methylene chloride, made basic with sodium carbonate and the product extracted into methylene chloride. Upon evaporation of the solvent there is obtained 16.6 g of oily title B product.

C.
1-(2-Dimethylaminoethyl)-5,7-dimethyl-1,2,3,4-tetrahydropyrido[2,3-d]pyrimidin-2-one A solution of methyl N-(3-cyano-4,6-dimethyl-2-pyridyl)-N-(2-dimethylaminoethyl)carbamate (14.8 g, 53 mmol) in glacial acetic (200 ml) containing platinum oxide catalyst (1.1 g) is hydrogenated in a Parr apparatus until two equivalents of hydrogen are taken up (20 hours). The catalyst is removed by filtration and the solvent evaporated to give a residue which is dissolved in water, made basic with sodium carbonate, and the crude product extracted into methylene chloride. This dried solution is evaporated to give a crude product (12.5 g) which is crystallized from cyclohexane to yield 7.2 g of pure title C product; m.p.: 139°–141° C.

EXAMPLE 5

1-(2-Dimethylaminoethyl)-5,7-dimethyl-1,2-dihydropyrido[2,3-d]pyrimidin-2-one

A solution of 1-(2-dimethylaminoethyl)-5,7-dimethyl-1,2,3,4-tetrahydropyrido[2,3-d]pyrimidin-2-one (5.0 g, 20 mmol) in chloroform (150 ml) containing activated manganese dioxide (15 g) is refluxed for 15 hours. The reaction mixture is filtered hot and the collected manganese dioxide re-extracted with hot chloroform. The combined organic extracts are evaporated and the residue crystallized from cyclohexane to yield 2.4 g of pure title product; m.p.: 137°–139° C.

EXAMPLE 6

1-(2-Dimethylaminoethyl)-3,5,7-trimethyl-1,2,3,4-tetrahydropyrido[2,3-d]pyrimidin-2-one A. Ethyl 3-(2-Dimethylaminoethylamino)-3-imino-propionate To a solution of N,N-dimethyl-1,2-diaminoethane (8.8 g, 0.1 mmol) in absolute ethanol (40 ml) is added ethyl 3-ethoxy-3-iminopropionate hydrochloride (20.0 g, 0.1 mmol). After stirring at ambient temperature for 16 hours, evaporated solvent and dissolved residue in water, made basic with sodium carbonate and extracted product into methylene chloride. This solution is evaporated to dryness to give 17 g of crude viscous title A product.

B. Ethyl 2-(2-Dimethylaminoethylamino)-4,6-dimethylnicotinate

A solution of crude ethyl 3-(2-dimethylaminoethylamino)-3-iminopropionate (15.3 g, 50 mmol) and pentane-2,4-dione (7.7 ml, 75 mmol) in dry benzene (80 ml) is refluxed for 18 hours. This solution is dried over anhydrous sodium sulfate and evaporated to give 18.4 g of crude title B product.

C.
2-(2-Dimethylaminoethylamino)-3-hydroxymethyl-4,6-dimethylpyridine

To a suspension of lithium aluminum hydride (3.5 g, 92 mmol) in dry tetrahydrofuran (160 ml) is added dropwise a solution of crude ethyl 2-(2-dimethylaminoethylamino)-4,6-dimethylnicotinate (18.5 g, 70 mmol) in dry tetrahydrofuran (100 ml) under a nitrogen atmosphere. Reaction mixture is refluxed for 1½ hours, cooled, quenched with saturated sodium sulfate solution filtered, dried and evaporated to give 15.0 g of crude title C product.

D.
2-(2-Dimethylaminoethylamino)-4,6-dimethyl-nicotinaldehyde

A solution of crude 2-(2-dimethylaminoethylamino)-3-hydroxymethyl-4,6-dimethylpyridine (15.0 g, 67 mmol) in methylene chloride (300 ml) containing a suspension of activated manganese dioxide (35 g) is refluxed for 5 hours. The solution is filtered hot and the manganese dioxide re-extracted with hot methylene chloride. The combined extracts are filtered through charcoal and evaporated to give 12.0 g of crude title D product.

E. Methyl N-(2-Dimethylaminoethyl)-N-(3-carboxaldehyde-4,6-dimethyl-2-pyridyl)carbamate A solution of crude 2-(2-dimethylaminoethylamino)-4,6-dimethylnicotinaldehyde (6.8 g, 30 mmol) in dry benzene (70 ml) containing methyl chloroformate (3.6 ml, 46 mmol) and triethylamine (6.7 ml, 48 mmol) is refluxed for three hours and then additional quantities of methyl chloroformate (1.2 ml, 15 mmol) and triethylamine (2.2 ml, 15 mmol) are added and the reaction mixture refluxed for an additional two hours. The cooled reaction is diluted with diethyl ether, the salts filtered, and the ethereal solution washed with water, dried, filtered through charcoal and evaporated to give 5.2 g of crude title E product.

F.
1-(2-Dimethylaminoethyl)-3,5,7-trimethyl-1,2,3,4-tetrahydropyrido[2,3-d]pyrimidin-2-one To a solution of monomethylamine gas (6.0 g, 19 mmol) in absolute ethanol (30 ml) is added 6 N ethanolic HCl (9.0 ml, 54 mmol) and then crude methyl N-(2-dimethylaminoethyl)-N-(3-carboxaldehyde-4,6-dimethyl-2-pyridyl)carbamate (5.2 g, 18 mmol) in absolute ethanol (20 ml). To this solution, cooled in an ice bath, is added sodium cyanoborohydride (0.8 g, 13 mmol). The mixture is allowed to stir and warm-up over 16 hour period. Concentrated hydrochloric acid is added until acidic and then the solvent is evaporated and the residue dissolved in water. Washed aqueous solution with methylene chloride, made basic with sodium carbonate and extracted product into methylene chloride. This solution is dried, filtered through charcoal and evaporated to 3.6 g of crude product. Crystallization of this product from cyclohexane yielded pure title E product (1.8 g); m.p.; 105°–107° C.

What is claimed is:
1. Compounds having the formulae:

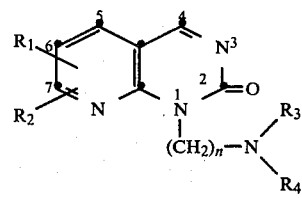

(I)

and

-continued

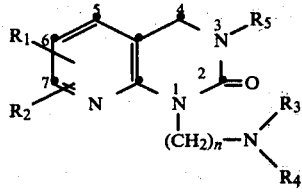

wherein:
R₁ and R₂ are independently hydrogen, haloloweralkyl, loweralkyl, loweralkoxy;
R₃ and R₄ are independently hydrogen, loweralkyl, cycloloweralkyl, or R₃ and R₄ may be joined, together with the nitrogen to which they are attached to form a piperazine ring or an N-loweralkyl piperazine ring;
R₅ is hydrogen or lower alkyl;
n is 2–5; and,
the physiologically acceptable salts thereof.

2. Compounds of claim 1 wherein n=2.
3. Compounds of claim 2 wherein R₁ is in the 5-position and R₂ is in the 7-position.
4. Compounds of claim 3 which are:
1-(2-diisopropylaminoethyl)-5,7-dimethyl-1,2-dihydropyrido[2,3-d]pyrimidin-2-one; or
1-(2-dimethylaminoethyl)-5,7-dimethyl-1,2-dihydropyrido[2,3-d]pyrimidin-2-one.
5. Compounds of claim 3 wherein R₅ is hydrogen.
6. Compounds of claim 5 which are:
1-(2-diisopropylaminoethyl)-5,7-dimethyl-1,2,3,4-tetrahydropyrido[2,3-d]pyrimidin-2-one; or
1-(2-dimethylaminoethyl)-5,7-dimethyl-1,2,3,4-tetrahydropyrido[2,3-d]pyrimidin-2-one.
7. Compounds of claim 3 wherein R₅ is loweralkyl.
8. Compounds of claim 7 which are:
1-(2-diisopropylaminoethyl)-3,5,7-trimethyl-1,2,3,4-tetrahydropyrido[2,3-d]pyrimidin-2-one; or
1-(2-dimethylaminoethyl)-3,5,7-trimethyl-1,2,3,4-tetrahydropyrido[2,3-d]pyrimidin-2-one.

* * * * *